United States Patent [19]

Satoh et al.

[11] 4,115,538
[45] Sep. 19, 1978

[54] ASSAY KIT FOR CAMP AND/OR CGMP AND METHOD OF USING THE SAME

[75] Inventors: Tomokazu Satoh; Junichi Takezawa; Akira Kuninaka, all of Choshi; Miyuki Honma; Michio Ui, both of Sapporo, all of Japan

[73] Assignee: Yamasu Shoyu Kabushiki Kaisha, Japan

[21] Appl. No.: 766,509

[22] Filed: Feb. 7, 1977

[30] Foreign Application Priority Data

Feb. 12, 1976 [JP] Japan .................................. 51-14665

[51] Int. Cl.$^2$ ...................... G01N 33/16; A61K 43/00; B65D 81/32
[52] U.S. Cl. ...................... 424/1; 23/230 B; 206/569
[58] Field of Search .............................. 424/1, 1.5, 12; 23/230 B, 223; 206/569

[56] References Cited
PUBLICATIONS

Wehmann et al., Endocrinology, vol. 90, No. 1, Jan., 1972, pp. 330–335.
Fujimoto et al., Chemical Abstracts, vol. 83, No. 17, Oct. 27, 1975, p. 221, Abstract No. 143973u.
Katoh et al., Chemical Abstracts, vol. 83, No. 1, Jul. 7, 1975, p. 385, Abstract No. 4254x.
Goldberg, Chemical Abstracts, vol. 86, No. 21, May 23, 1977, p. 197, Abstract No. 152305s.

Primary Examiner—Benjamin R. Padgett
Assistant Examiner—Christine M. Nucker
Attorney, Agent, or Firm—Wenderoth, Lind & Ponack

[57] ABSTRACT

An assay kit for assaying adenosine-3',5'-cyclic monophosphate, which is herein referred to as cAMP, guanosine-3',5'-cyclic monophosphate, which is herein referred to as a cGMP, or both; and said assay kit comprising,
  a container of Reagent 1 comprising succinyl cAMP tyrosine methyl ester; succinyl cGMP tyrosine methyl ester; succinyl cAMP tyrosine methyl ester and succinyl cGMP tyrosine methyl ester in admixture or both succinyl cAMP tyrosine methyl ester and succinyl cGMP tyrosine methyl ester in separate containers, said esters labelled with radioactive iodine;
  a container of Reagent 2 comprising an anti-cAMP serum, an anti-cGMP serum, an anti-cAMP and anti-cGMP serum in admixture or both anti-cAMP serum and anti-cGMP serum in separate containers;
  a container of Reagent 3 comprising an imidazole buffer solution of 0.1 M or higher concentration;
  a container of Reagent 4 comprising a material for separation;
  a container of Reagent 5 comprising a solution of succinic anhydride in an organic solvent;
  a container of Reagent 6 comprising an organic tertiary amine; and
  a container of Reagent 7 comprising a standard solution of cAMP, cGMP, cAMP and cGMP in admixture or both cAMP and cGMP in separate containers.

12 Claims, 2 Drawing Figures

ASSAY KIT FOR CAMP AND/OR CGMP AND METHOD OF USING THE SAME

BACKGROUND OF THE INVENTION

This invention relates generally to radioimmunoassay techniques and more particularly to assay kits for the assay of adenosine-3',5'-cyclic monophosphate and/or guanosine-3',5'-cyclic monophosphate by a radioimmunoassay method and to a method of using the assay kits.

In recent years, adenosine-3',5'-cyclic monophosphate (hereinafter referred to by the abbreviation cAMP) has been widely studied as a mediator of hormone action, and with respect to guanosine-3',5'-cyclic monophosphate (hereinafter referred to by the abbreviation cGMP), also, its physiologic action is being clarified. Particularly from the observation that the contents of cAMP and cGMP within a living body are apt to change when that living body is in an unphysilogic or pathological state such as a diseased state, the great importance of the assay of the contents of these cyclic nucleotide within a living body not only in basic medical research but also in diagonosis, prevention, and treatment of diseases in the field of clinical medicine is being recognized.

For example, the assays of cAMP and cGMP in samples taken from living bodies such as leucocytes from asthmatic patients, skin of psoriasis patients, blood platelets of thrombocytosis patients, blood and urine of pseudohypoparathyroidism patients, blood and urine of muscular dystrophy patients, and cerebrosphinal fluid of manic-depressive patients are effective in the diagnosis and treatment of these diseases. Furthermore, the clarification of the interrelationships between the results of these assays and numerous diseases is expected hereafter.

However, the methods known heretofore for the assay of cAMP and cGMP cannot be said to be satisfactory on the point of sensitivity and, furthermore, have been accompanied by problems of time and economy in the preparation of samples from organisms. For instance, a nonspecific factor(s) which hinder(s) the assay is present in a sample from an organism, and in order to remove this effect, it is considered necessary to dilute the sample to a high dilution ratio. This dilution, however, further lowers the concentration of the cAMP and cGMP which are present in minute quantities and therefore difficult to assay from the beginning. As a result, this further lowered concentration becomes less than the lower limit of measurability, whereby quantitative measurements are rendered even more difficult.

Furthermore, since there is originally a great difference between the contents within an organism of cAMP and cGMP, a single sample preparation cannot be used as a common sample. In this connection, the compositions and minimum limiting quantities for measuring of cAMP and cGMP assay kits presently sold on the market are as set forth in Tables 1 and 2.

Table 1.

| | cAMP assay kits on the market | |
|---|---|---|
| Product | Composition | Min.Limiting quantity for measuring (p mol.*/tube) |
| A | ①Tris/EDTA buffer ②cAMP standard solution ③Tritium-labeled cAMP ④Binding protein ⑤Material for separation | 0.2 |
| B | ①cAMP standard solution ②Iodine-labeled cAMP ③cAMP antibody | 0.05 |
| C | ①cAMP standard solution ②Iodine-labeled cAMP ③cAMP antibody ④Antibody for separation | 1 |
| D | ①Acetate buffer ②cAMP standard solution ③Tritium-labeled cAMP ④Binding protein ⑤Separation filter ⑥Buffer for washing filter | 1 |

*picomol.

Table 2.

| | cGMP assay kits on the market | |
|---|---|---|
| Product | Composition | Min.limiting quantity for measuring (p mol./tube) |
| E | ①cGMP standard solution ②Iodine-labeled cGMP ③cGMP antibody | 0.05 |
| F | ①cGMP standard solution ②Iodine-labeled cGMP ③cGMP antibody ④Antibody for separation | 0.05 |
| G | ①Acetate buffer ②Tritium-labeled cGMP ③cGMP standard solution ④Binding protein | 0.2 |

Thus, the minimum limiting quantities for measuring of cAMP and cGMP by means of these kits on the market are 0.05 p mol./tube or higher in all cases, whereby it is not possible by using these kits to achieve the object of ultramicro-assay of cAMP and cGMP which will inevitably become a requirement hereafter.

One known method for improving the measurement sensitivity of radioimmunoassay is the method wherein cAMP is subjected to succinylation thereby to increase the affinity of the cAMP for its antibody, as proposed in Analytical Biochemistry, Volume 56, p.394 through p.407, (1973). In this method, a process (A) in an organic solvent system which comprises dissolving a freeze-dried test specimen of a sample of an organism and 4-morpholino-N,N'-dicyclohexylcarboxamidine in pyridine and adding to the resulting solution a solution of succinic anhydride in dioxane thereby to carry out a succinylation reaction and a process (B) in an aqueous solution system which comprises adding succinic anhydride powder and triethylamine to an aqueous solution of the test specimen thereby to carry out a succinylation reaction are proposed.

The process (A), however, is not practical because of difficulties such as the condition that the prepared form of the test specimen must be freeze-dried and the low efficiency of succinylation due to low solubility of the cAMP in the solvent. In the process (B), since the succinic anhydride is supplied in powder form, and also in consideration of the hydrolyzable nature of succinic anhydride in an aqueous solution system, it is essential to promote instantaneously the dissolution and diffusion of the succinic anhydride into the aqueous solution of the test specimen by a vigorous shaking action in order to cause the succinylation reaction to progress with high efficiency. Accordingly, in addition to the difficulty of handling the powder, equipment for this shaking action is necessary. The simultaneous assay of a large number of test specimens is particularly difficult by this process, which is unsuitable for practice by a simple assay kit. By this process, furthermore, dialysis is used as an expedient for separating the free cAMP and the cAMP bound with the antibody after the antigen-antibody reaction, but special equipment is necessary for the dialysis, and this process has not been satisfactory as a general assay process.

SUMMARY OF THE INVENTION

It is an object of the present invention to solve the various problems accompanying the known cAMP and cGMP assay kits as described above.

It is another object of the invention to provide assay kits which make possible the simultaneous ultramicroassay of cAMP and cGMP with very simple means.

These and other objects of the present invention will become apparent from a consideration of the following specification and claims.

The cAMP and cGMP assay kits according to this invention comprise combinations of the following seven reagents.

Reagent 1. Succinyl cAMP tyrosine methyl ester labeled with radioactive iodine ([*I] ScAMP-TME), succinyl cGMP tyrosine methyl ester, succinyl cAMP tyrosine methyl ester and succinyl cGMP tyrosine methyl ester in admixture or both succinyl cAMP tyrosine methyl ester and succinyl cGMP tyrosine methyl ester in separate containers labeled with radioactive iodine ([*I] ScGMP-TME).

Reagent 2. Anti-cAMP serum, anti-cGMP serum anti-cAMP and anti-cGMP serum in admixture or both anti-cAMP serum and anti-cGMP serum in separate containers.

Reagent 3. Imidazole buffer solution of 0.1 M or higher.

Reagent 4. Material for separation.

Reagent 5. Solution in an organic solvent of succinic anhydride.

Reagent 6. Organic tertiary amine.

Reagent 7. Standard solution (s) of cAMP, cGMP, cAMP and cGMP in admixture or both cAMP and cGMP in separate containers.

The nature, utility, and further features of this invention will be apparent from the following detailed description beginning with a consideration of general features of the invention and concluding with results of experiments and specific examples of practice and of use.

DETAILED DESCRIPTION

A principal feature of an assay kit of this invention is that it has Reagents 5 and 6 as succinylation reagents and that the Reagent 3 is adopted as a buffer solution for antigen-antibody reaction.

More specifically, we have discovered for the first time that the succinylation reaction of cAMP and cGMP within a test specimen can progress with amply good efficiency in a mixed system of water and an organic solvent. A first important feature of this invention is that, on the basis of this discovery, succinic anhydride is rendered into the force of a solution in an organic solvent, whereby its handling is simplified. We have found that, by merely blending the organic solvent solution of succinic anhydride of Reagent 5 and the organic tertiary amine of Reagent 6 immediately prior to the assay and adding the resulting blended liquid to the cAMP and/or cGMP standard solution or a sample containing cAMP and/or cGMP, the cAMP and/or cGMP can be succinylated instantaneously and, moreover, thoroughly, and the affinity thereof to the antiserum can be remarkably increased.

Moreover, as a result of the improvement of the sensitivity, it becomes possible to amply dilute the sample prior to the reaction with the antiserum. Accordingly, it becomes possible to actually remove the cause of inhibition of the reaction in the sample, and not only is the measurement error greatly reduced, but, as the liquid quantity is increased by dilution, repeated measurement of the same sample and the simultaneous measurement of the cAMP and cGMP contents of the same sample are made possible. Furthermore, body fluids such as blood, cerebrospinal fluid, and urine and acid extraction products of body tissues can be used as they are as samples.

In addition, we have newly discovered that, by using an imidazole buffer of 0.1 M or higher at the time of antigen-antibody reaction instead of an acetate buffer, a phosphate buffer, or a citrate buffer, which have generally heretofore been used, the antigen-antibody reaction can be remarkably stabilized, and the effect of the succinylation reagent in inhibiting this reaction can be completely eliminated. This discovery is utilized as a second important feature of the assay kits of this invention.

Thus, the cAMP and cGMP assay kits of this invention make possible for the first time ultramicro-assay of cAMP and cGMP in a sample by a very simple and convenient procedure with combinations of these new reagents. In this connection, the minimum limiting quantities for measuring of cAMP and cGMP of the assay kits of this invention is approximately 0.006 p mol/tube in either case.

This invention will now be described with respect to specific quantities and specific reagents.

Reagent 5

The quantity of the succinic anhydride in Reagent 5 is of the order of 2 to 6 mg., preferably 3.5 to 4.5 mg., for 100 $\mu$l of the sample. We have found that, if the succinic anhydride quantity is excessive, the succinic anhydride will precipitate out in the succinylation reaction system, and there will be a possibility of its inhibiting the antigen-antibody reaction.

Any organic solvent which stably dissolves succinic anhydride and, at the same time, does not have a deleterious effect on the antigen-antibody reaction is suitable for use in accordance with this invention. Specific examples of such solvents are pyridine, dioxane, acetone, acetonitrile, dimethylsulfoxide, diethyleneglycoldimethylether, hexamethylphosphorictriamide, tetrahydropyrane, and methyl cellosolve acetate. Dioxane and hexamethylphosphorictriamide, particularly, can be effectively utilized.

Reagent 6

For the organic tertiary amine of Reagent 6, one which is readily rendered homogeneous with Reagent 5, does not impart a deleterious effect to the antigen-antibody reaction, and promotes the succinylation reaction is suitable. Specific examples of effective organic tertiary amines are triethylamine and 4-morpholino-N,N'-dicyclohexylcarboxamidine. The quantity in which this tertiary amine is used is, in the case of triethylamine, for example, 15 µl or less, preferably 10 µl or less for 100 µl of the sample. If an excessive quantity is used, the pH will rise, and the succinylation reaction will be inhibited.

The mixing ratio of the Reagents 5 and 6 is determined on the basis of the kinds of organic solvent and organic tertiary amine used. For example, in the case where dioxane is used as the organic solvent and triethylamine is used as the organic tertiary amine in the succinylation of 1 p mol. of cAMP in blood plasma by means of succinic anhydride, the relationships between the quantities of these substances and the degree of succinylation of the cAMP have been found to be as set forth in Table 3. The degree of succinylation in this case was determined by the cellogel electrophoresis method.

Table 3.

| Composition of succinylation reagents | | | Degree of succinylation (%) |
|---|---|---|---|
| Succinic anhydride (mg) | Triethylamine (µl) | Dioxane (µl) | |
| 0 | 0 | 100 | 0 |
| 0.5 | 1.25 | 98.75 | 45 |
| 1.0 | 2.5 | 97.5 | 70 |
| 2.0 | 5.0 | 95.0 | 100 |
| 4.0 | 10.0 | 90 | 100 |

Table 3 indicates that, in the case of this system, the use of a solution of 4 mg. of succinic anhydride dissolved in 90 µl. of dioxane (approximately 4.4% solution of succinic anhydride) as Reagent 5 and 10 µl. of triethylamine as Reagent 6 is suitable. The degrees of succinylation of cAMP and cGMP in various samples with the use of Reagents 5 and 6 prepared in this manner were measured and found to be as set forth in Table 4.

Table 4.

| Kind of sample | | Degree of succinylation (%) |
|---|---|---|
| Acid extraction product of — | | |
| rat lung | 10 mg/100µl | 99.4 |
| " cerebrum | " / " | 98.3 |
| " liver | " / " | 97.5 |
| " heart | " / " | 97.2 |
| Rabbit plasma | 100 µl | 94.0 |
| " cerebrospinal fluid | " | 100.0 |
| Human plasma | " | 100.0 |

Thus, by the simple procedure of mixing Reagents 5 and 6 into the samples, the succinylation of cAMP and cGMP is accomplished efficiently irrespective of the kind of sample.

While the method of preparing the sample is not particularly subject to any restrictions, the optimal method, ordinarily, is to prepared fluids such as blood, cerebrospinal fluid, and urine as they are or as solutions, to which EDTA has been added, and tissues in general as extracts by means of extractants such as solutions in water or in hydrophilic organic solvents of acids such as hydrochloric acid, perchloric acid, and trichloroacetic acid,) and alkalis (such as barium hydroxide + zinc sulfate), and as hydrophilic organic solvents.

There are no particular restrictions on the conditions of the succinylation reaction, the conditions of room temperature and a reaction time of 5 to 60 minutes ordinarily being sufficient.

Reagent 3

The buffer in accordance with the present invention is an aqueous solution of imidazole the pH of which has been set to a desired value in the range of 5 to 8 by addition thereto of an acid, such as hydrochloric acid, which does not have the deleterious effect on the antigen-antibody reaction.

(1) Minimum limiting quantity for measuring

| Kind of buffer solution | Min.limiting quantity for measuring f mol.*/tube |
|---|---|
| Imidazole buffer solution | 6.25 |
| Acetate buffer solution | 25 |
| Phosphate buffer solution | 25 |
| Citrate buffer solution | 25 |

*femtomol (2) Antigen-Antibody reaction (degree of reaction of Reagents 1 and 2)

| Kind of buffer solution | Degree of Antigen-Antibody reaction (%) |
|---|---|
| Imidazole buffer solution | 65.4 |
| Acetate buffer solution | 68.7 |
| Phosphate buffer solution | 47.0 |
| Citrate buffer solution | 38.2 |

(3) Plasma sample dilution effect

With the use of an imidazole buffer solution reasonable results of cAMP 15.5 p mol./ml. of plasma and 7.5 p mol./0.5 ml. of plasma are obtained. However, with the use of an acetate buffer solution, the results of cAMP 14.5 p mol./ml. of plasma and 10.5 p mol./0.5 ml. of plasma, and with the use of a citrate buffer solution, the results of cAMP 30 p mol./ml. of plasma and 20 p mol./0.5 ml. of plasma, which are unreasonable results without occurrence of dilution effect, are obtained in some cases.

(4) Abnormality in the assay of protein-rich sample

The antigen-antibody reaction degrees in the case where a plasma not containing cAMP and cGMP, that is, a plasma obtained after a plasma has been left standing at 37° C for 24 hours after sampling thereby to completely decompose cAMP and cGMP, is used as a sample and in the case where distilled water is used as a sample are theoretically equal. With the imidazole buffer solution, the reaction degrees in the two cases are equal, but with the acetate buffer solution, the reaction degrees are 73.9% for the former case and 68.7% for the latter case, there being a difference of more than 5%.

From these results, it may be supposed that, in the case where a sample containing proteins such as plasma is used, and the concentrations of cAMP and cGMP are low, e.g. at a number of tens of f mol./tube, a value which is lower than the actual concentration is obtained with an acetate buffer solution. Furthermore, it was found in one instance with a citrate buffer solution that, with respect to a reaction degree of 38.2% in the former case, that in the latter case was 34.5%.

Thus, Reagent 3 has the characteristic of enhancing sensitivity of the assay and, moreover, stabilizing the antigen-antibody reaction and, further, has an effective action such that accurate values can be obtained even with respect to samples from which proteins have not been removed.

A concentration of the imidazole buffer solution of 0.1 M or higher is a requisite. If the concentration is less than 0.1 M, abnormal values as described in item (4) above will occur. Furthermore, the pH value should be in the range of 5 to 8, the optimum pH being in the vicinity of 6.5. If the pH is lower than 5 the buffer action will be weak, while if it is higher than 8, the [*I] ScAMP-TME and [*I] ScGMP-TME of Reagent 1 will decompose. In this connection, imidazole is known to promote the enzymatic action of phosphodiesterase. In conformance with necessity, fluctuations in the assay values due to the action of any phosphodiesterase remaining in the test specimen or antiserum can be prevented by adding beforehand a phosphodiesterase inhibitor such as EDTA or theophylline.

Reagent 1

The [*I] ScAMP-TME and/or [*I] ScGMP-TME of Reagent 1 are/is ordinarily prepared as a solution in a buffer solution such as an imidazole buffer solution or as freeze-dried powder with a possible stabilizer therefor. Reagent 1 is combined in the kit in conformance with the purpose of the assay. For example, for the assay of only cAMP or cGMP, a [*I] ScAMP-TME or [*I] ScGMP-TME corresponding respectively thereto is independently selected and combined in the kit, while for the assay of both cAMP and cGMP, corresponding [*I] ScAMP-TME and [*I] ScGMP-TME are combined in the kit in separated state or in a mixed form. For simultaneous assay of the [*I] ScAMP-TME and [*I] ScGMP-TME in mixed state, it is advantageous to use distinctively the different types of radioactive iodine, for example, $^{125}I$ and $^{131}I$, thereby to afford measurement with respect to each.

Reagent 2

The anti-cAMP serum and/or anti-cGMP serum of Reagent 2 can be prepared by an ordinary method. For example, a solution in an imidazole buffer solution or in an acetate buffer solution of an antiserum obtained through the use of an animal such as a rabbit by a method according to the method of Steiner et al, *Journal of Biological Chemistry*, No. 247, p.1106 through p.1113, (1972), can be used. The potency of the antiserum has, for example, a binding rate of 50% or higher with respect to the total radioactivity of the added [$^{125}$I]cAMP-TME or [$^{125}$I]cGMP-TME when 0.03 μl (1:9900) of antiserum of a certain rabbit is used for this measurement system. The combination of the kind of the antiserum of Reagent 2 is in accordance with that of Reagent 1.

For the antigen-antibody reaction, ordinary conditions can be directly adopted, it being suitable to carry out the reaction at 1° to 5° C for 6 to 48 hours, preferably 12 to 24 hours.

Reagent 4

The material for separation of Reagent 4 is used for the purpose of separating the cAMP or cGMP bound with the antibody, namely antigen-antibody complex, from free cAMP or cGMP. Examples of materials suitable for the separation are dextran-coated charcoal, ammonium sulfate, polyethylene glycol, and antigammaglobulin serum, which are ordinarily used in radioimmunoassay, as they are or as in a dispersion or solution thereof in water or a buffer solution. Other materials are applicable, of course, provided that they function to achieve the same purpose.

The conditions of separation are determined in accordance with the kind of material for separation. For example, as a result of causing 100 μl. of [$^{125}$I] ScAMP-TME, 100 μl. of a 0.3-M imidazole buffer solution of an anti-cAMP serum, pH 6.5, and 100 μl of a 0.3-M imidazole buffer solution, pH 6.5, to react in ice water for 16 hours, adding to this reaction system 500 ml. of a suspension in water of dextran-coated charcoal(DCC), subjecting the resulting batch to centrifugal separation, and thereafter measuring the radioactivity of the resulting supernatant which comprises the bound cAMP, namely the antigen-antibody complex, the percent rates, B/T(%), of the radioactivity of the antigen-antibody complex relative to the tool radioactivity under various conditions were as set forth in Table 5.

Table 5

| Experiment No. DCC (mg/500μl) | 1* | 2** | 3*** |
|---|---|---|---|
| 1.25 | 52.5 | 50.0 | 51.0 |
| 2.5 | 51.5 | 49.0 | 50.0 |
| 5.0 | 52.5 | 50.0 | 50.5 |

*Experiment 1. Centrifugal separation immediately after addition of DCC
**Experiment 2. Centrifugal separation 30 min. after addition of DCC
***Experiment 3. Centrifuging immediately after addition of DCC and separating 30 min. thereafter.

From these results, it is apparent that a quantity of the DCC of 2.5 mg. is sufficient and that the separability after addition of the activated carbon is stably sustained for at least 30 minutes after the addition.

Reagent 7

The standard solution of the cAMP and/or cGMP of Reagent 7 is a solution, in water or in an imidazole buffer solution, of a free acid of cAMP and/or cGMP or such a soluble salt thereof with such as sodium, potassium, or the like as will not have a deleterious effect on the antigen-antibody reaction, in a concentration suited to the formation of a standard curve.

Use of the kit

The assay kit of this invention is a combination of 7 types of reagents.

The reagents may be used in accordance with ordinary procedure for radioimmunoassay of cAMP an cGMP. More specifically, the procedure comprises:

(1) mixing Reagents 5 and 6 to prepare a succinylating agent;

(2) adding this agent to the test specimen and to a standard solution prepared from Reagent 7 and mixing these materials thereby to cause a succinylation reaction;

(3) diluting each of these materials with Reagent 3;

(4) thereafter mixing each of the process materials with Reagent 1 and further with Reagent 2 thereby to cause concurrently antigen-antibody reactions in each mixture;

(5) separating the formed antigen-antibody complex by means of Reagent 4; and (6) measuring the radio-activity thereof, the content of cAMP or cGMP in the test specimen being determined from the standard curve of the B/T(%) value formed by the standard solution.

By the use of the assay kit according to this invention the cAMP and the cGMP coexisting in a sample can be simultaneously succinylated. For this reason, a sample which has been succinylated in one stage can be halved, and radioimmunoassay of cAMP and cGMP can be carried with respect to each half. If, for Reagent 1, a mixture of, for example, [$^{125}$I] ScAMP-TME and [$^{131}$I] ScGMP-TME is used, not only the succinylation but also the radioimmunoassay can be carried out is the same tube.

In order to indicate more fully the nature and utility of this invention, the following specific examples of practice and examples of use are set forth, it being understood that these examples are presented as illustrative only and are not intended to limit the scope of the invention.

EXAMPLE 1

A cAMP assay kit for 75 test specimens comprising:
Reagent 1 comprising $^{125}$I] ScAMP-TME (1 μci/8 ml,
0.3 M imidazole buffer solution, pH 6.5);
Reagent 2 comprising domestic rabbit anti-cAMP serum/
8 ml., 0.3 M imidazole buffer solution pH 6.5;
Reagent 3 comprising 1.5 M imidazole buffer solution,
pH 6.5, 12 ml, which is to be diluted to one-fifth concentration at the time of use;
Reagent 4 comprising charcoal 200 mg., bovine serum
albumin 200 mg., suspension of dextran 30 mg. in distilled water 20 ml., which is to be diluted to one-half concentration at the time of use;
Reagent 5 comprising succinic anhydride 400 mg./dioxane 9 ml.;
Reagent 6 comprising triethylamine 1 ml.; and
Reagent 7 comprising 320 mol. of cAMP (sodium salt)/water 1 ml., which is the stock standard solution.

EXAMPLE 2

A cGMP assay ket for 75 test specimens comprising:
Reagent 1 comprising [$^{125}$I] ScGMP-TME (1 μci/8 ml.,
0.3 M imidazole buffer solution, pH 6.5);
Reagent 2 comprising domestic rabbit anti-cGMP serum/
8ml., 0.3 M imidazole buffer solution, pH 6.5;
Reagents 3, 4, 5, and 6 respectively the same as those in Example 1; and
Reagent 7 comprising cGMP (sodium salt) 320 p mol/water 1 ml., which is to be the stock standard solution.

EXAMPLE 3

A kit for the assay of both cAMP and cGMP for 75 test specimens comprising, in combination, Reagents 1 and 2 of Example 2 and Reagents 1, 2, 3, 5, and 6 of Example 1, Reagent 4 of Example 1 in doubled quantity, and, as Reagent 7, 320 p mol. of cAMP (sodium salt) as well as 320 p mol. of cGMP (sodium salt) dissolved in 1 ml. of water.

EXAMPLE 4

A kit for the simultaneous assay of cAMP and cGMP for 75 test specimens comprising a Reagent 1 comprising a 0.3-M imidazole buffer solution, of pH 6.5, 8 ml. containing [$^{125}$I] ScAMP-TME 1μci and [$^{131}$I] ScGMP-TME 1 μci, a Reagent 4 which is the same as that in Example 4, and Reagents 2, 3, 5, 6, and 7 which are respectively the same as those in Example 3.

EXAMPLE 5

A kit for the simultaneous assay of cAMP and cGMP for 75 test specimens comprising a Reagent 3 comprising a 1.5-M imidazole buffer containing EDTA of 12.5 mM, pH 6.5, 24 ml., and Reagents 1, 2, 4, 5, 6, and 7 which are respectively the same as those in Example 4.

EXAMPLE 6

A kit for the assay of both cAMP and cGMP for 75 test specimens comprising a Reagent 5 which is succinic anhydride 400 mg. in hexamethylphosphorictriamide 9 ml. and Reagents 1, 2, 3, 4, 6, and 7 which are respectively the same as those in Example 3.

Example of USE 1

The following procedure of use can be applied to the case where blood plasma is the sample, and the cAMP assay kit of Example 1 is used.
1. Reagents 5 and 6 are mixed in a ratio by volume of 9 : 1 thereby to prepare a succinylating reagent.
2. Reagent 3 (diluted to one-fifth concentration prior to use), distilled water, and the succinylating reagent are mixed in a ratio by volume of 8 : 1 : 1 thereby to prepare a buffer for dilution.
3. 100 μl. of Reagent 7 is placed in a small test tube and mixed with 100 μl. of the succinylating reagent. The resulting mixture is allowed to stand at room temperature for 10 minutes, and then 800 μl. of Reagent 3 is added thereto thereby to prepare 3.2 mol./100 μl. of a succinyl cAMP standard solution 1 ml.(No.I).
4. Into each of 9 small test tubes (Nos.II through X), 500 μl. of the buffer for dilution prepared in step (2) is poured, and 500 μl. of the succinyl cAMP standard solution of 3.2 p mol./100 μl. prepared in step (3) is added to the small test tube No.II and mixed with the contents thereof. Thereafter, dilution to successively halve the concentration is carried out thereby to prepare succinyl cAMP standard solutions of respective concentrations of 3,200 f mol., 1,600 f mol., 800 f mol., 400 f mol., 200 f mol., 100 f mol., 50 f mol., 25 f mol., 12.5 f mol., and 6.25 f mol./100 μl.
5. 100 μl of a plasma is placed in a small test tube, and 100 μl of the succinylating reagent is added thereto and mixed therewith. The resulting mixture is allowed to stand at room temperature for 10 minutes, and thereafter 800 μl. of Reagent 3 is added thereto thereby to prepare a plasma sample. In this connection, the quantity used of Reagent 3 is so determined that the succinic acid concentration at the time of antigen-antibody reaction will become of an order such that it will not impair the reaction (approximately 0.15% or less).
6. Small test tubes are prepared as indicated below.
For total count : 3 tubes, Nos. 1 through 3
For blank : 2 tubes, Nos. 4, 5
For zero : 2 tubes, Nos. 6, 7

For standard solution: 20 tubes, Nos. 8 through 27 For plasma sample: 2 tubes, Nos. 28, 29

7. 100 μl. of Reagent 1 is poured into each of the above test tubes.
8. 100 μl. of the buffer for dilution is added to each of the test tubes for total count (Nos.1, 2, and 3), for blank (Nos. 4 and 5), and for zero (Nos. 6 and 7).
9. 100 μl. of the succinylated cAMP standard solutions Nos. I through X is added to each of the test tubes Nos. 8 through 27.
10. 100 μl. of succinylated plasma is added to the test tubes Nos. 28 and 29 for plasma sample.
11. 100 μl. of Reagent 2 is added into each of the test tubes Nos. 6 through 29 for zero, for standard solution, and for plasma sample, and, after mixing of the resulting mixtures, these mixtures are allowed to stand in ice water for a period of from 12 to 24 hours (18 hours in the instant example).
12. 100 μl. of 0.3-M imidazole buffer solution is added into each of the test tubes Nos. 1 through 5 for total count and for blank. Then after mixing, the resulting mixtures are allowed to stand similarly as in step (11) above.
13. 500 μl. of Reagent 4 (diluted to one-half concentration prior to use) is added to each of the test tubes other than those for total count, which test tubes are then subjected to centrifugal separation at 3,000 r.p.m. for 5 minutes.
14. 500 μl. of water is added to each of the test tubes for total count, the contents of which are then mixed.
15. 500 μl. of the supernatant is taken from each test tube and transferred to each of test tubes for radioactivity measurement.
16. The radioactivity of each supernatant is measured.
17. The average value (BL) of the blank count is subtracted from each of the average value (T) of the total count and the average value B of the count of each standard solution, and the binding rate [B/T (%)] is calculated from the following equation.

$$B/T (\%) = \frac{(B) - (BL)}{(T) - (BL)} \times 100 (\%)$$

In the instant example, the results of measurement and calculation were as set forth in Table 6.

Table 6

| Average value | | cpm | cpm −BL | B/T % |
|---|---|---|---|---|
| Blank count av. value (BL) | | 300 | — | — |
| Total count av. value | | 9109 | 8809 | 100 |
| Count for zero av. value | | 6065 | 5765 | 65.4 |
| Std. solution count av. value | | 5806 | 5506 | 62.5 |
| " | 6.25 f mol. | | | |
| " | 12.5 " | 5543 | 5243 | 59.5 |
| " | 25 " | 5069 | 4769 | 54.1 |
| " | 50 " | 4600 | 4300 | 48.8 |
| " | 100 " | 3614 | 3314 | 37.6 |
| " | 200 " | 2837 | 2537 | 28.8 |
| " | 400 " | 1992 | 1692 | 19.2 |
| " | 800 " | 1391 | 1091 | 12.4 |
| " | 1600 " | 888 | 588 | 6.7 |
| " | 3200 " | 620 | 320 | 3.6 |
| Plasma av. value | | 3119 | 2819 | 32.0 |

Figure 1:
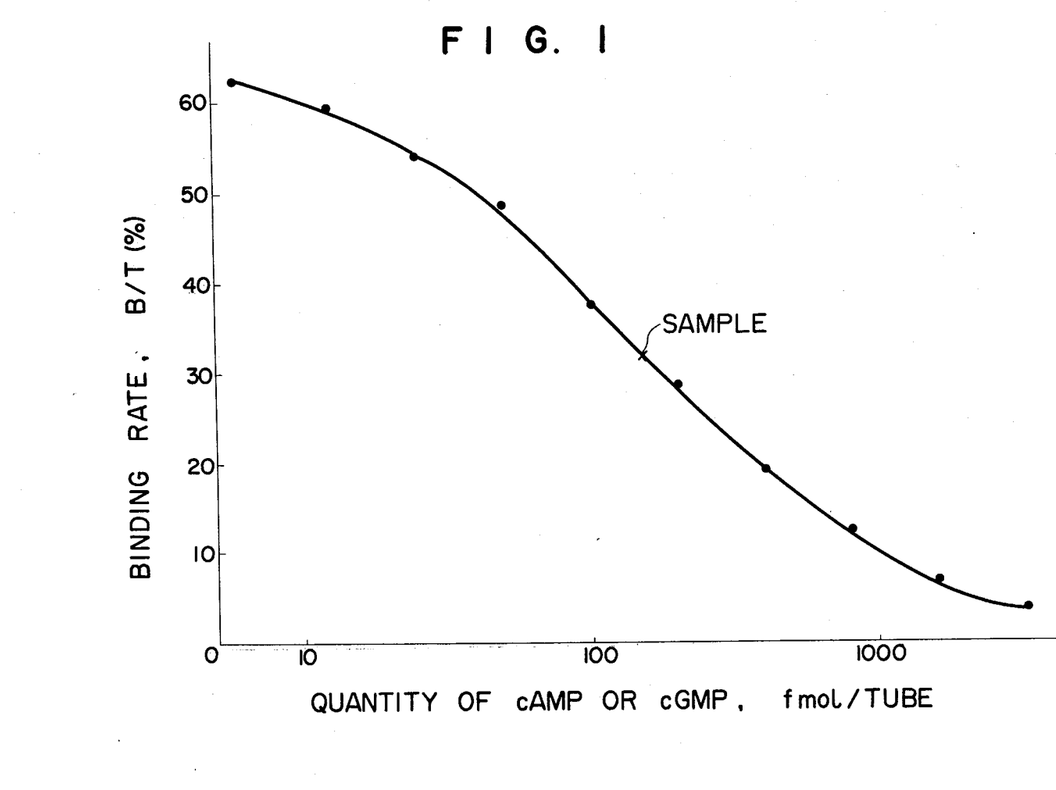
FIGS. 1 and 2 are graphs showing standard curves respectively plotted on the basis of Example of Use 1 and Example of Use 2, the ordinate and abscissa of each graph respectively representing binding rate (B/T, %) with the antibody and quantity of cAMP or cGMP.

18. A standard curve is plotted on a semilogarithmic graph with the ordinate respresenting the binding rates of the various standard solutions and the abscissa representing their concentrations (the standard curve of the instant example being as shown in FIG. 1).
19. Through the use of this standard curve, the cAMP concentration of the plasma sample is determined from its B/T (%). In this instant example, 150 f mol./tube corresponds to 15,000 f mol./ml. plasma.

EXAMPLE OF USE 2

In the case where plasma is used as a sample, and for the kit for cGMP assay, that of Example 2 is used, the step (1) through (16) of Examples of Use 1 are carried out exactly as set forth. Binding rates are calculated from measured values similarly as in Step (17) in Example of Use 1. The results of the instant example are shown in Table 7.

Table 7

| Average value | | cpm | cpm −BL | B/T % |
|---|---|---|---|---|
| Blank count av. value (BL) | | 200 | — | — |
| Total count av. value | | 9885 | 9685 | 100.0 |
| Count for zero av. value | | 6540 | 6340 | 65.5 |
| Std. solution count av. value | | 6296 | 6096 | 62.9 |
| " | 6.25 f mol. | | | |
| " | 12.5 " | 5821 | 5621 | 58.0 |
| " | 25 " | 5058 | 4858 | 50.2 |
| " | 50 " | 4033 | 3833 | 39.6 |
| " | 100 " | 2870 | 2670 | 27.6 |
| " | 200 " | 1866 | 1666 | 17.2 |
| " | 400 " | 1288 | 1088 | 11.2 |
| " | 800 " | 846 | 646 | 6.7 |
| " | 1600 " | 563 | 363 | 3.7 |
| " | 3200 " | 428 | 228 | 2.4 |
| Plasma av. value | | 4113 | 3933 | 40.6 |

Figure 2:
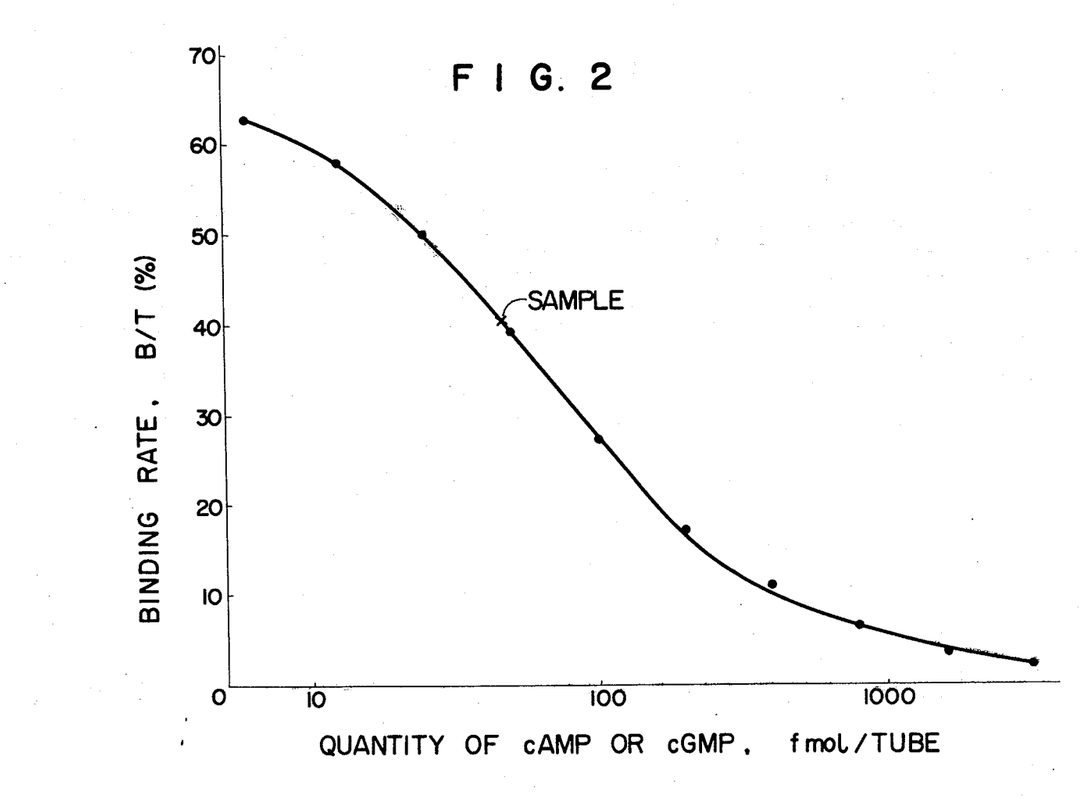

18. A standard curve is plotted similarly as in Example of Use 1.

The standard curve of the instant example is as shown in FIG. 2.

19. By the use of this standard curve, the cGMP concentration of the plasma sample is determined from its B/T (%), whereupon 47 f mol./tube to 4,700 f mol./ml. plasma.

We claim:
1. An assay kit for assaying adenosine-3′,5′-cyclic monophosphate, which is herein referred to as cAMP, guanosine-3′,5′-cyclic monophosphate, which is herein referred to as cGMP, or both; and said assay kit comprising,
a container of Reagent 1 comprising succinyl cAMP tyrosine methyl ester; succinyl cGMP tyrosine methyl ester; succinyl cAMP tyrosine methyl ester and succinyl cGMP tyrosine methyl ester in admixture or both succinyl cAMP tyrosine methyl ester and succinyl cGMP tyrosine methyl ester in separate containers, said esters labeled with radioactive iodine;
a container of Reagent 2 comprising anti-cAMP serum; anti-cGMP serum; anti-cAMP and anti-cGMP serum in admixture or both anti-cAMP serum and anti-cGMP serum in separate containers;
a container of Reagent 3 comprising an imidazole buffer solution of 0.1 M or higher concentration;
a container of Reagent 4 comprising a material for separation;
a container of Reagent 5 comprising a solution of succinic anhydride in an organic solvent;
a container of Reagent 7 comprising a standard solution of cAMP; cGMP; cAMP and cGMP in admix- ture or both cAMP and cGMP in separate containers.

2. An assay kit as claimed in claim 1 in which the pH value of the imidazole buffer solution of Reagent 3 is from 5 to 8.

3. An assay kit as claimed in claim 1 in which the imidazole buffer solution of Reagent 3 contains a phosphodiesterase inhibitor.

4. An assay kit as claimed in claim 1, in which the organic solvent for succinic anhydride of Reagent 5 is dioxane.

5. An assay kit as claimed in claim 1 in which the organic tertiary amine of Reagent 6 is a member selected from the group consisting of 4-morpholino-N,N'-dicyclohexylcarboxamidine and triethylamine.

6. An assay kit as claimed in any one of claim 1 in which the material for separation of Reagent 4 is a member selected from dextran-coated charcoal, dextran-coated charcoal dispersion, ammonium sulfate, ammonium sulfate solution, polyethylene glycol, polyethylene glycol solutin, anti gamma-globulin serum and anti gamma-globulin serum solution.

7. An assay kit as claimed in claim 1, in which the organic solvent for succinic anhydride of Reagent 5 is a member selected from the group consisting of pyridine, dioxane, acetone, acetonitrile, dimethylsulfoxide, diethylene glycol dimethyl ether, hexamethylphosphorictriamide, tetrahydropyrane, and methyl cellosolve acetate.

8. An assay kit according to claim 7 wherein the organic solvent is dioxane.

9. An assay kit according to claim 7 wherein the organic solvent is hexamethylphosphorictriamide.

10. A method of using an assay kit for assaying cAMP, cGMP or both which comprises:
    mixing Reagent 5 comprising a solution of succinic anhydride in an organic solvent and Reagent 6 comprising an organic tertiary amine;
    adding the resulting mixture respectively to a test specimen and Reagent 7 comprising a standard solution of cAMP; cGMP; cAMP and cGMP in admixture or both cAMP and cGMP in separate containers thereby to succinylate the cAMP, cGMP or both;
    diluting the resulting products respectively with Reagent 3 comprising an imidazole buffer solution of 0.1 M or higher concentration and thereafter mixing the same respectively with Reagent 1 comprising cAMP tyrosine methyl ester, succinyl cGMP tyrosine methyl ester or both;
    mixing the resulting mixtures respectively with Reagent 2 comprising anti-cAMP serum, anti-cGMP serum, or both thereby to cause an antigen-antibody reaction in each of the mixtures;
    adding respectively to the resulting product Reagent 4 comprising a material for separation thereby to separate antigen-antibody complex thus formed; and
    measuring the radioactivity of the antigen-antibody complex thereby to accomplish ultramicro-assay of cAMP, cGMP or both.

11. A method of using an assay kit for assaying cAMP, cGMP or both as claimed in claim 10 in which the mixing of Reagent 5 and Reagent 6 is carried out immediately prior to the addition of the resulting mixture thereof to the test specimen and Reagent 7.

12. In a method for assaying cAMP, cGMP or both contained in organisms wherein cAMP, cGMP or both in a sample taken from an organism are succinylated, the succinylated cAMP, cGMP or both are caused to undergo an antigen-antibody reaction with anti-cAMP serum, anti-cGMP serum or both in the presence of succinyl cAMP tyrosine methyl ester, succinyl cGMP tyrosine methyl ester labeled with radioactive iodine, or both which undergo an antigen-antibody reaction with the anti-cAMP serum, anti-cGMP serum or both, the antigen-antibody complex thus formed is separated, and the radioactivity of the antigen-antibody complex or free antigen is measured thereby to determine the content of cAMP, cGMP or both in the organism based on the radioactivity thus measured, the improvement which comprises the use, as a reaction medium for the antigen-antibody reaction, of an imidazole buffer solution of 0.1 M or higher concentration.

* * * * *

UNITED STATES PATENT AND TRADEMARK OFFICE
CERTIFICATE OF CORRECTION

PATENT NO. : 4,115,538
DATED : September 19, 1978
INVENTOR(S) : Tomokazu Satoh, Junichi Takezawa, Akira Kuninaka, Miyuki Honma and Michio Ui It is certified that error appears in the above-identified patent and that said Letters Patent are hereby corrected as shown below:

Claim 1, between lines 24 and 25, insert the following:

-- a container of Reagent 6 comprising an organic tertiary amine; and --;

Signed and Sealed this

Twenty-fourth Day of July 1979

[SEAL]

Attest:

Attesting Officer

LUTRELLE F. PARKER
Acting Commissioner of Patents and Trademarks